United States Patent
Young

(10) Patent No.: US 10,182,829 B2
(45) Date of Patent: Jan. 22, 2019

(54) SURGICAL INSTRUMENT AND SYSTEM OF SURGICAL INSTRUMENTS

(71) Applicant: DePuy Ireland Unlimited Company, Cork (IE)

(72) Inventor: Duncan Young, Hebden Bridge (GB)

(73) Assignee: DEPUY IRELAND UNLIMITED COMPANY, Cork (IE)

( * ) Notice: Subject to any disclaimer, the term of this patent is extended or adjusted under 35 U.S.C. 154(b) by 601 days.

(21) Appl. No.: 14/845,717

(22) Filed: Sep. 4, 2015

(65) Prior Publication Data

US 2017/0065286 A1    Mar. 9, 2017

(51) Int. Cl.
*A61B 17/15* (2006.01)
*A61B 17/14* (2006.01)

(52) U.S. Cl.
CPC .......... *A61B 17/157* (2013.01); *A61B 17/142* (2016.11)

(58) Field of Classification Search
CPC ..... A61B 17/15–17/158; A61B 17/142; A61B 17/144
See application file for complete search history.

(56) References Cited

U.S. PATENT DOCUMENTS

| | | |
|---|---|---|
| 4,860,735 A | 8/1989 | Davey |
| 6,090,114 A | 7/2000 | Matsuno |
| 7,104,997 B2 | 9/2006 | Lionberger |
| 7,704,253 B2 | 4/2010 | Bastian |
| 7,867,236 B2 | 1/2011 | Hodorek |
| 7,959,635 B1 | 6/2011 | Bonutti |
| 8,021,368 B2 | 9/2011 | Haines |
| 2003/0045883 A1* | 3/2003 | Chow ............... A61B 17/15 606/88 |
| 2005/0192588 A1* | 9/2005 | Garcia ............. A61B 17/155 606/88 |
| 2006/0004373 A1 | 1/2006 | Ondrla et al. |

(Continued)

FOREIGN PATENT DOCUMENTS

| | | |
|---|---|---|
| EP | 0104732 A1 | 4/1984 |
| EP | 0415837 A2 | 7/1991 |

(Continued)

OTHER PUBLICATIONS

European Search Report for EPO Patent App. No. 15179613.3-1654, dated Dec. 23, 2015, 7 pages.

(Continued)

*Primary Examiner* — Matthew Lawson

(57) ABSTRACT

A cutting guide assembly comprises a mounting block having a guide surface into which may be mounted an articulated mounting arm. The mounting arm has a first post which is retained in the mounting block and a second post. A cutting tool attachment component is provided to attach the cutting tool to the cutting guide assembly. The cutting tool attachment component has a first surface against which the saw blade can be retained for oscillation around an axis of oscillation, and a shaft which cooperates with the second post such that the longitudinal axis of the shaft is collinear with the axis of oscillation of the saw blade. When the saw blade is retained against the first surface, the plane of oscillation is parallel to, and displaced from, the guide surface of the mounting block.

15 Claims, 10 Drawing Sheets

(56) References Cited

U.S. PATENT DOCUMENTS

2006/0009796 A1* 1/2006 Carusillo ............. A61B 17/157
606/178
2014/0171952 A1* 6/2014 Maxson ............. A61B 17/1739
606/87
2016/0051268 A1* 2/2016 Seitlinger .......... A61B 17/1764
606/88

FOREIGN PATENT DOCUMENTS

| WO | WO 9325157 A1 | 12/1993 |
| WO | WO 0071035 A1 | 11/2000 |
| WO | WO 0191647 A1 | 2/2002 |
| WO | WO 03013371 A1 | 2/2003 |

OTHER PUBLICATIONS

UK Search Report for corresponding App. No. GB1414171.7 dated Feb. 19, 2015, 4 pages.

* cited by examiner

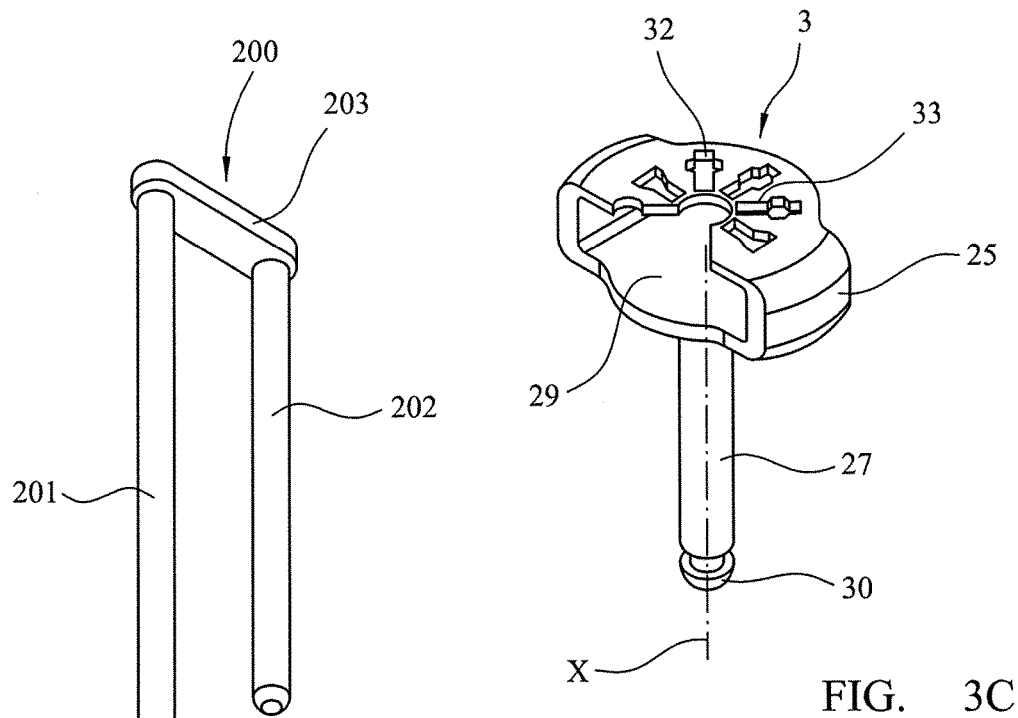
FIG. 3C
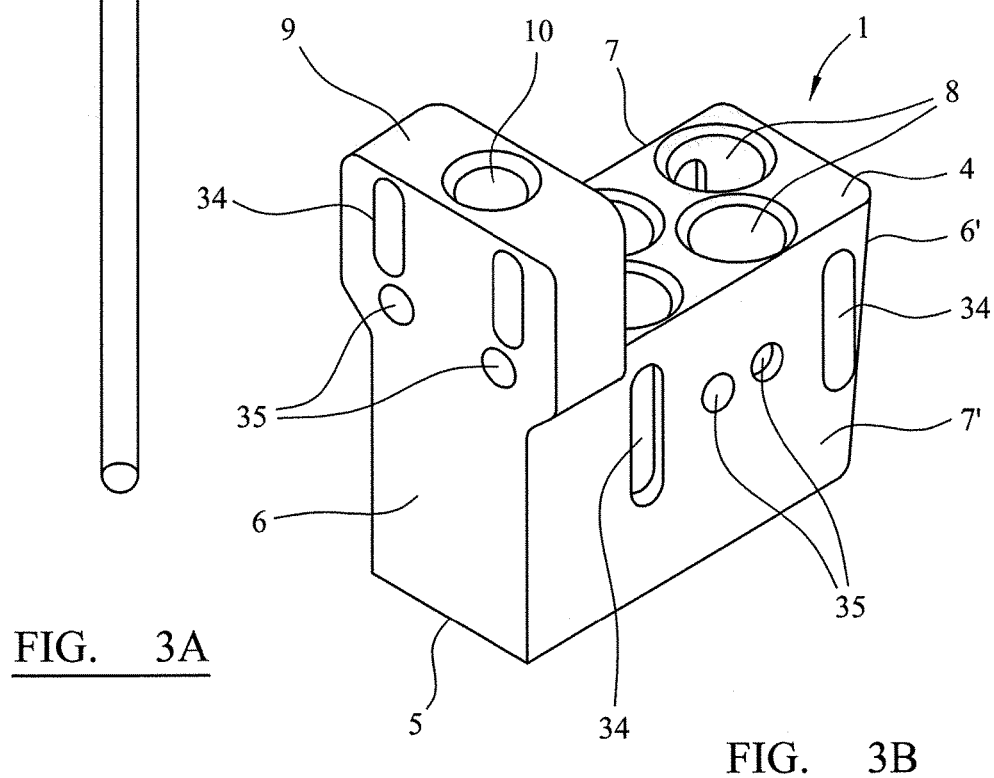
FIG. 3A
FIG. 3B

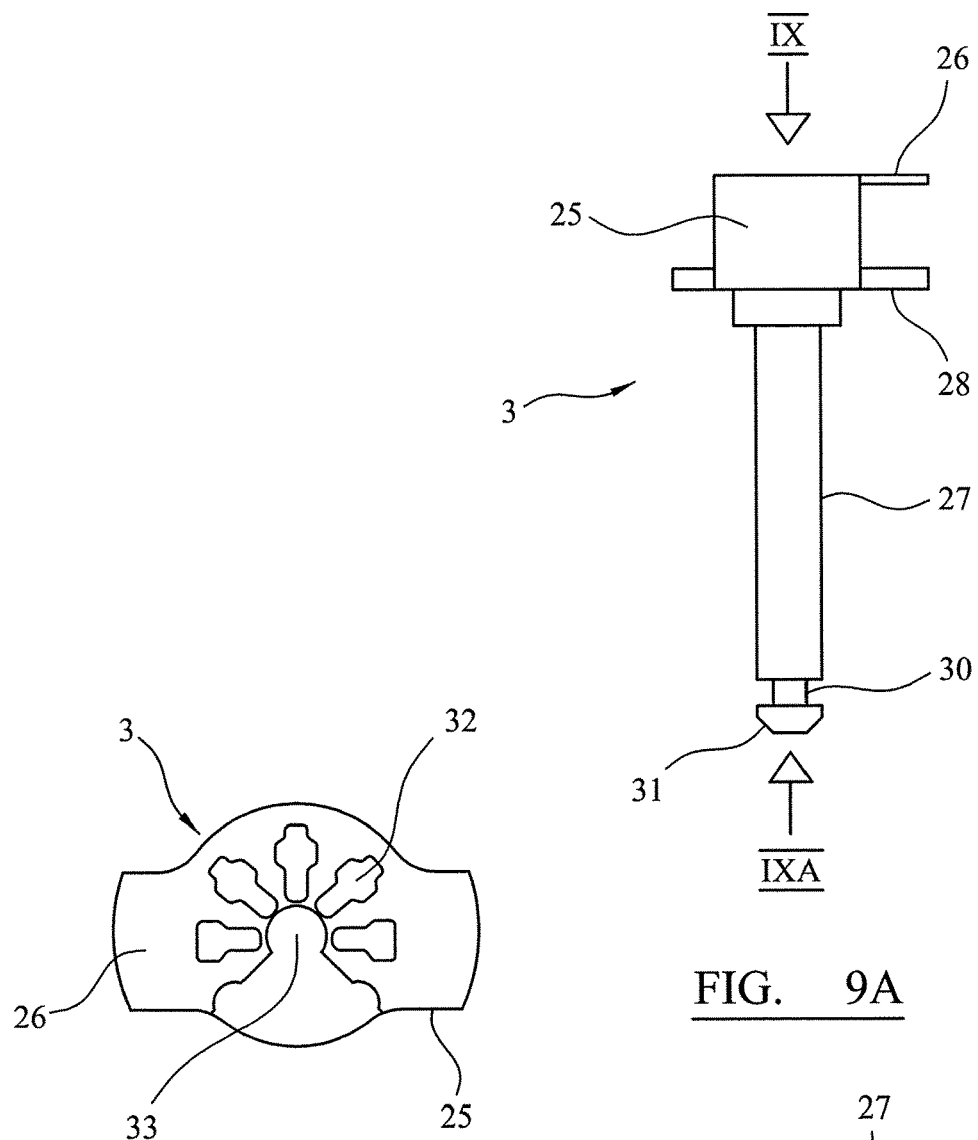
FIG. 9A
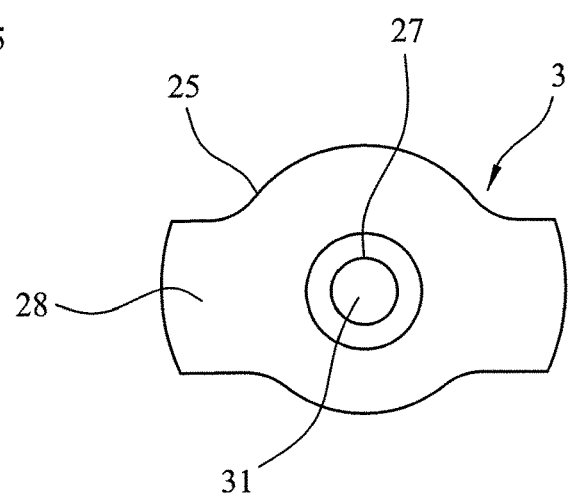
FIG. 9B
FIG. 9C

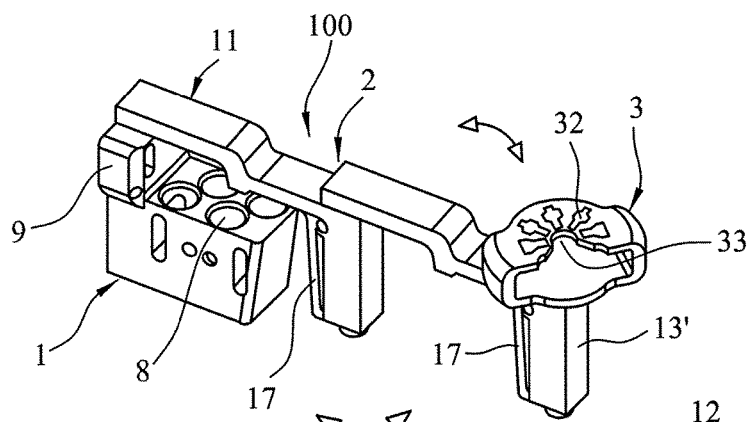
FIG. 10A
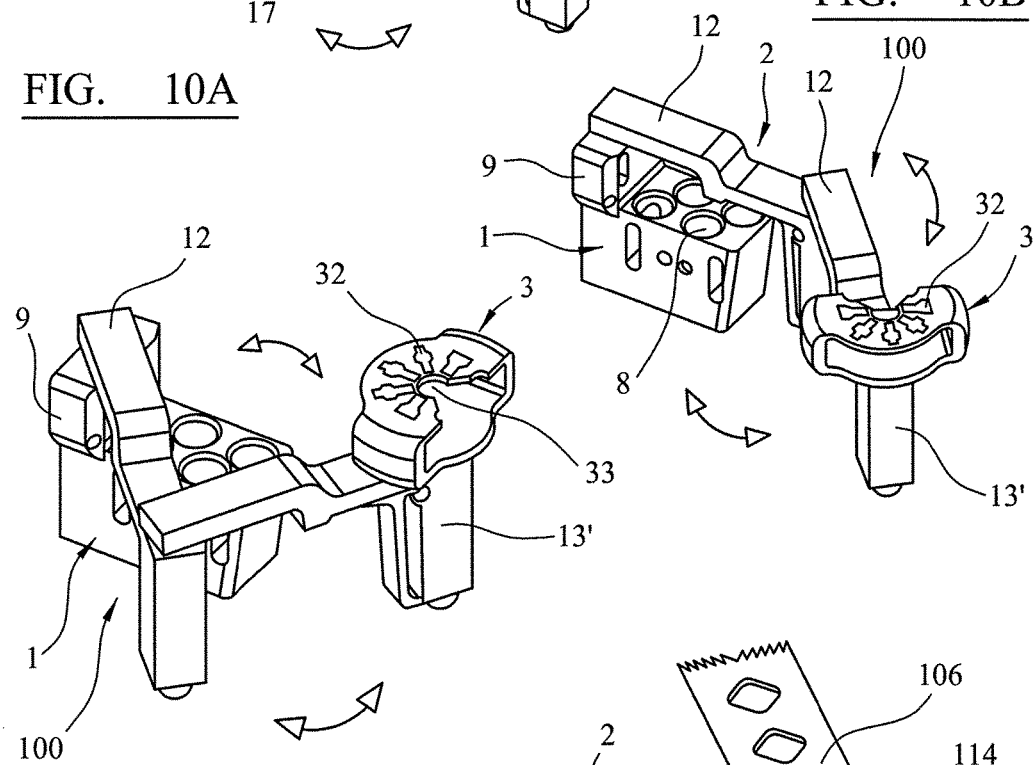
FIG. 10B
FIG. 10C
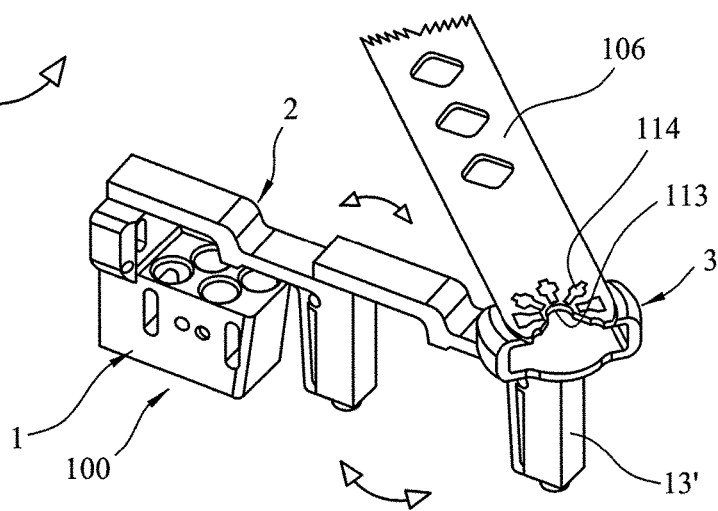
FIG. 10D

SURGICAL INSTRUMENT AND SYSTEM OF SURGICAL INSTRUMENTS

BACKGROUND

The present invention relates to surgical instruments and in particular to surgical instruments for guiding saws and other cutting tools used in bone surface preparation.

Existing cutting tools have a saw blade with a cutting edge which is typically serrated at its distal end. The saw blade is secured to the cutting tool at its proximal end for oscillation in a side-to-side motion and driven by a driving mechanism such as a shaft coupled to a motor. To cut or resect a bone, the saw is oscillated at high speed around an axis of oscillation which causes the blade to cut through the bone.

To facilitate accurate cutting of the bone, many surgical instruments are fixed in a known position relative to a patient. One way of doing this uses a cutting block. Cutting blocks are typically affixed to a patient's bone in a position such that they can guide cutting and resection of the bone surface for receiving an implant.

Existing cutting blocks may include a guide, recess or cutting groove for the saw blade in order to correctly position and guide the cutting tool during the surgical procedure.

Although this takes some skill and practice a surgeon is able to produce a cut that is reasonably accepted as predictable.

Such cutting blocks can exhibit a number of limitations or disadvantages:

Friction against the surface of the cutting block can lead to wear particles being produced;
Friction can generate heat that leads to thermal necrosis of the bone and also to risk of injury or burns to the surgeon;
A lack of visibility of the saw as it approaches the bone;
Saw blade excursion and thickness may be limited by the dimensions of the recess;
Some surgeons prefer to use narrow blades, while some use wider blades known as "whale tails", but not all of these blades are compatible with all recesses;
Recesses can become wider as they are used which reduces the accuracy over time;
In saw slots which are not a constant depth, the engagement length between blade and block changes as the blade moves along the cut, reducing and increasing the amount of play;
Cutting blocks can become damaged over time;
Surgeon preferences vary which requires manufacturers to develop and manufacture a number of designs and variants;
Each recess is made very accurately which increases costs; and
Cutting blocks require replacement significantly often.

SUMMARY OF THE INVENTION

According to the present invention, there is provided a cutting guide assembly for guiding a saw blade of a cutting tool. The saw blade is configured for oscillation in a plane of oscillation, and around an axis of oscillation. The guide assembly comprises a mounting block, a mounting arm, a first post, a second post and a cutting tool attachment component for attaching the cutting tool to the cutting guide assembly. The mounting block has a guide surface. The mounting arm has a first end and a second end. The first post has a longitudinal axis and extends from the first end of the mounting arm in a direction perpendicular to the mounting arm. The first post is configured to be retained in the mounting block in a direction perpendicular to the guide surface. The second post extends parallel to the first post at the second end. The cutting tool attachment component has a first surface against which the saw blade can be retained for oscillation around the axis of oscillation, and a shaft, having a longitudinal axis, extending in a direction away from, and perpendicular to, the first surface. The shaft is configured to cooperate with the second post such that the longitudinal axis of the shaft is collinear with the axis of oscillation of the saw blade, and such that, when the saw blade is retained against the first surface, the plane of oscillation is parallel to, and displaced from, the guide surface of the mounting block.

This cutting guide assembly has the advantage of orienting a saw blade such that it consistently cuts into the bone surface to be prepared or resected in the direction required without direct contact with a guiding surface. With no direct cutting against a guide surface none of the problems identified above are encountered.

The mounting block may include an elongate retaining bore running through the block in a direction perpendicular to the guide surface so as to retain the first post in the mounting block in a direction perpendicular to the guide surface. The elongate retaining bore may be provide in a projection extending substantially orthogonal to the guide surface such that the retaining bore extends in a direction substantially perpendicular to the guide surface.

The second post may further include a longitudinal bore running along the longitudinal axis of the second post and configured to receive and retain the shaft of the cutting tool attachment member so that the longitudinal axis of the shaft is collinear with the axis of oscillation of the saw blade.

The shaft may include a circumferential groove provide towards the distal end of the shaft and the mounting arm may include a detent in the form of a spring-biased locking member provided adjacent the second post and having a lip that engages with the circumferential groove provided on the shaft.

The retaining bore may include at least one retaining mechanism for retaining the first post with the retaining bore at a predetermined position. The retaining means may be configured to engage a corresponding groove or recess on the first post.

The mounting arm may be articulated.

The mounting arm may comprise two or more substantially U-shaped mounting arm sections detachably coupled to each other to provide the articulations.

The mounting arm sections may be detachably coupled by means of cooperating posts and bores configured for relative rotational movement around a common axis.

The mounting arm sections may be secured together by means of a detent. The detent may be in the form of a spring-biased locking member provided on one U-shaped mounting arm section having a lip that engages with a circumferential groove provided on a cooperating post of another of the two or more U-shaped mounting arm sections.

The mounting block may comprise a plurality of alignment bores running through the mounting block from the guide surface and configured to receive and alignment rod of an alignment tool.

There may be four alignment bores which subtend different angles to a plane substantially orthogonal to the guide surface. The different angles may be less than 10° and more particularly may be any of angles 0°, 1°, 3°, 5° and 7°.

The mounting block may include a plurality of apertures for securing the mounting block to a bone surface by means of mounting projections.

The attachment component may comprise an attachment block defining the first surface and a second surface from which the shaft extends.

The attachment block may further define an internal cavity for receiving a portion of the cutting tool to attach the attachment component to the cutting tool.

The first surface may be configured to cooperate with clamping means provided on the cutting tool for retaining the proximal end of the saw blade against the first surface for oscillation about the axis of oscillation. The first surface may comprise a plurality of apertures for engaging with respective attachment means on the cutting tool.

The cutting guide assembly may be part of a kit that includes an alignment tool. The alignment tool may comprise a cross-piece and first and second substantially parallel alignment rods provided at the ends of the cross piece.

The first and second alignment rods may be of different lengths.

Alternatively, the alignment tool may comprise a single rod.

The alignment tool may include an ankle clamp.

According to another aspect of the invention, there is provided a surgical instrument system including a cutting guide assembly for guiding a saw blade of a cutting tool. The saw blade is configured for oscillation in a plane of oscillation, and around an axis of oscillation, and an alignment tool. The cutting guide assembly comprises a mounting block having a guide surface, a mounting arm having a first end and a second end, a first post, a second post and a cutting tool attachment component for attaching the cutting tool to the cutting guide assembly. The first post has a longitudinal axis that extends from the first end of the mounting arm in a direction perpendicular to the mounting arm; it is configured to be retained in the mounting block in a direction perpendicular to the guide surface. The second post extends parallel to the first post at the second end. The cutting tool attachment component has a first surface against which the saw blade can be retained for oscillation around the axis of oscillation, and a shaft, having a longitudinal axis, extending in a direction away from, and perpendicular to, the first surface and configured to cooperate with the second post such that the longitudinal axis of the shaft is collinear with the axis of oscillation of the saw blade, and such that, when the saw blade is retained against the first surface, the plane of oscillation is parallel to, and displaced from, the guide surface of the mounting block. The surgical instrument system also includes an alignment tool comprising a cross-piece and first and second substantially parallel alignment rods provided at the ends of the cross piece.

According to another aspect of the invention, there is provided a method of preparing the surface of a bone. The method includes the steps of locating a mounting block having a guide surface adjacent a bone surface to be prepared. An alignment tool is used to align the guide surface of the mounting block to a required plane of preparation. The aligned mounting block is secured adjacent the bone surface to be prepared. A mounting arm and alignment component and mounted to the mounting block. The attachment component is configured to attach a cutting tool, having a saw blade, such that saw blade can be retained for oscillation around an axis of oscillation in a plane of oscillation that is perpendicular to the axis of oscillation, the plane of oscillation being parallel to, and displaced from, the guide surface of the mounting block. The bone is cut to prepare the bone surface by means of the saw blade.

According to yet another embodiment of the invention, there is provided a cutting guide assembly for guiding a saw blade of a cutting tool, the saw blade being configured for oscillation in a plane of oscillation, and around an axis of oscillation. The guide assembly comprises a mounting block, a first post, a second post, a mounting arm and a cutting tool attachment component for attaching the cutting tool to the cutting guide assembly. The mounting block has a guide surface and an elongate retaining bore running through the block in a direction perpendicular to the guide surface. The mounting arm has a first end and a second end. The first post has a longitudinal axis and extends from the first end of the mounting arm in a direction perpendicular to the mounting arm such that the longitudinal axis of the first post extends in a direction perpendicular guide surface. The first post is retained in the elongate retaining bore of the mounting block such that the first post extends in a direction perpendicular to the guide surface. The second post extends parallel to the first post at the second end. The cutting tool attachment component, the cutting tool attachment component having a first surface against which the saw blade can be retained for oscillation around the axis of oscillation, and a shaft, having a longitudinal axis, extending in a direction away from, and perpendicular to, the first surface and configured to cooperate with the second post such that the longitudinal axis of the shaft is collinear with the axis of oscillation of the saw blade, and such that, when the saw blade is retained against the first surface, the plane of oscillation is parallel to, and displaced from, the guide surface of the mounting block.

BRIEF DESCRIPTION OF THE DRAWINGS

The invention will now be described, by way of example, only, with reference to accompanying drawings of which:

FIGS. 3A, 3B and 3C are isometric views of component parts of the surgical instrument system of FIG. 2, with FIG. 3A showing the alignment tool, FIG. 3B showing the mounting block of the cutting guide assembly, and FIG. 3C showing the cutting tool attachment member of the cutting guide assembly;

FIG. 9A is a side view of the cutting tool attachment member of the cutting guide assembly;

FIG. 9B is a plan view of the cutting tool attachment member of the cutting guide assembly in the direction of arrow IX of FIG. 9A;

FIG. 9C is an underside view of the cutting tool attachment member of the cutting guide assembly in the direction of arrow IXA of FIG. 9A;

FIGS. 10A to 10C are perspective view of the cutting guide assembly of the surgical instrument system of FIG. 1 illustrating the articulation of the mounting arm;

FIG. 10D is a perspective view of the cutting guide assembly of the surgical instrument system of FIG. 1 illustrating the articulation of the mounting arm, but with a saw blade in place;

DETAILED DESCRIPTION OF THE DRAWINGS

Figure 1A:
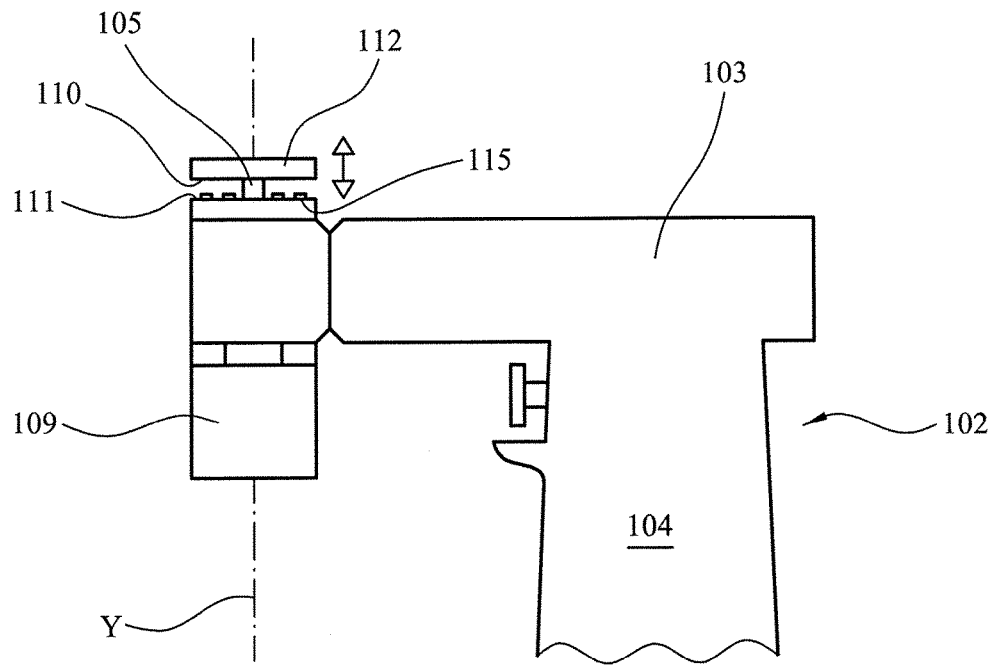
FIG. 1A is a schematic side view of a cutting tool of the prior art without a saw blade.

A cutting guide assembly 100 comprise a mounting block 1, a mounting arm 2 and a cutting tool attachment component 3.

The cutting guide assembly 100 is configured to mount and guide a cutting tool 102 thereon during bone surface preparation, to aid bone surface preparation and resection.

The cutting tool 102 can be any suitable cutting tool known in the art and, as such, need not be described in any great detail herein except as is relevant to the present invention.

Figure 1B:
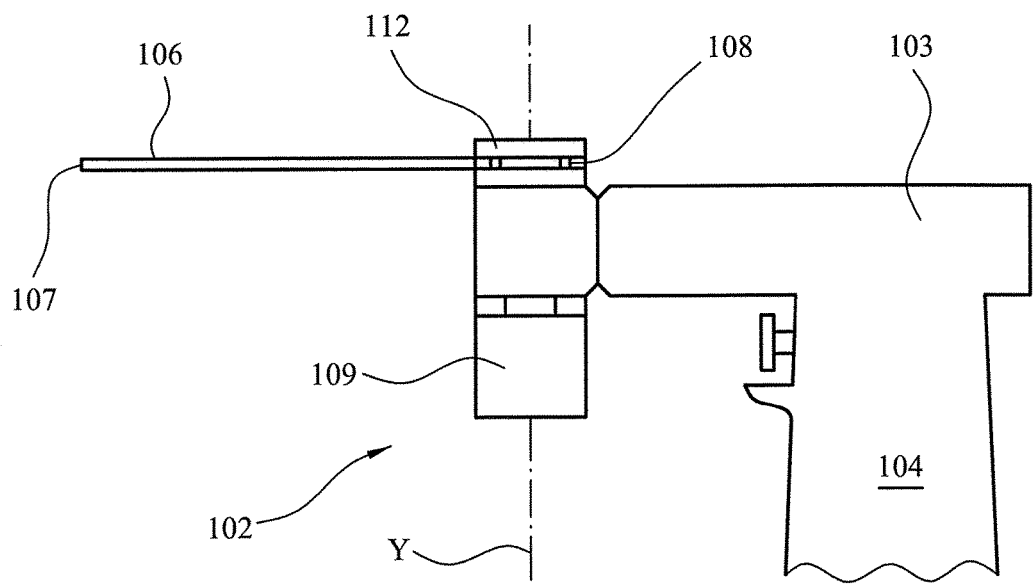
FIG. 1B is a schematic side view of a cutting tool of FIG. 1A with the saw blade in situ.
Figure 2:
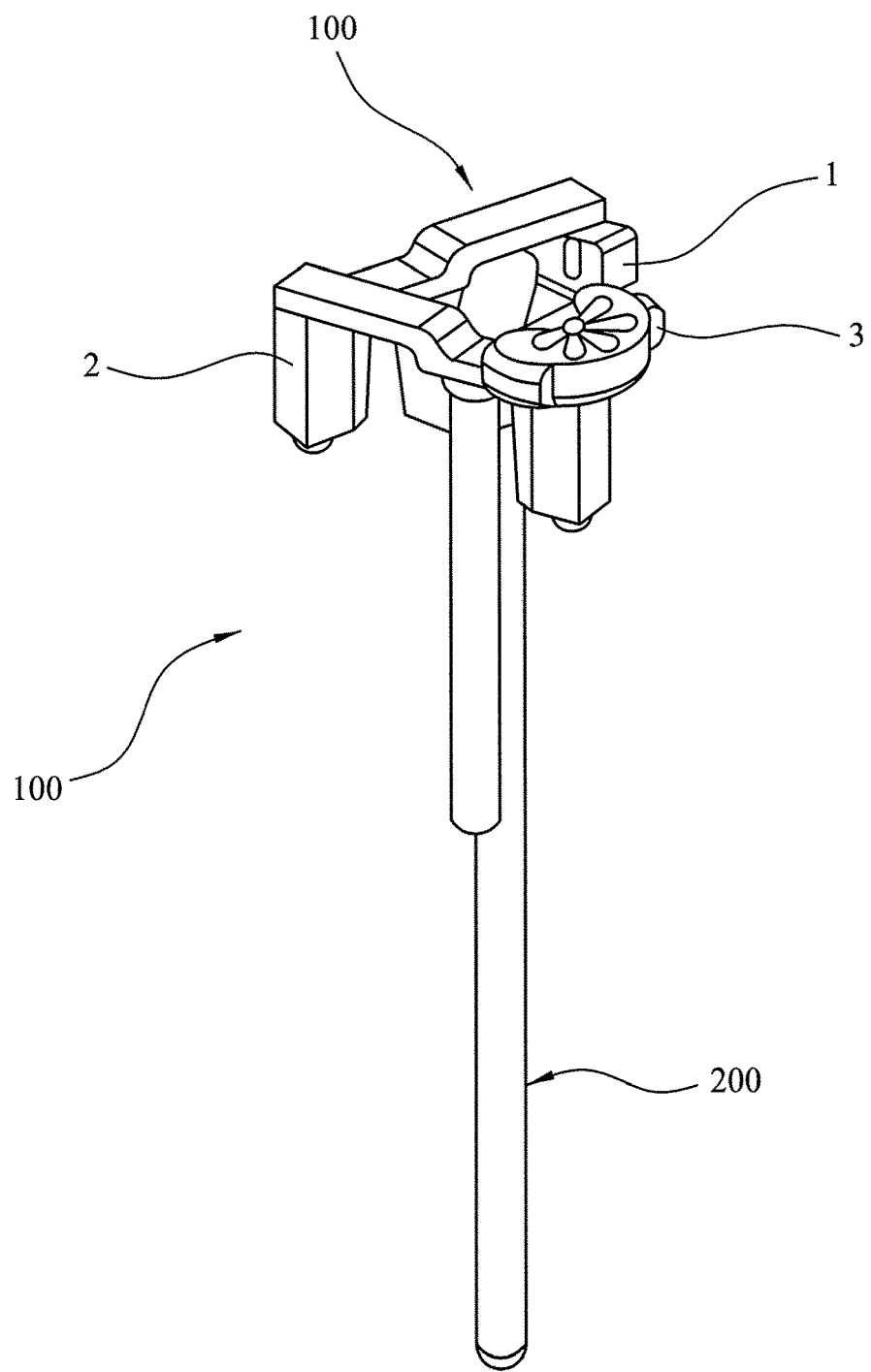
FIG. 2 is a perspective view of a surgical instrument system including an alignment tool and a cutting guide assembly.
Figures 4A, 4B:
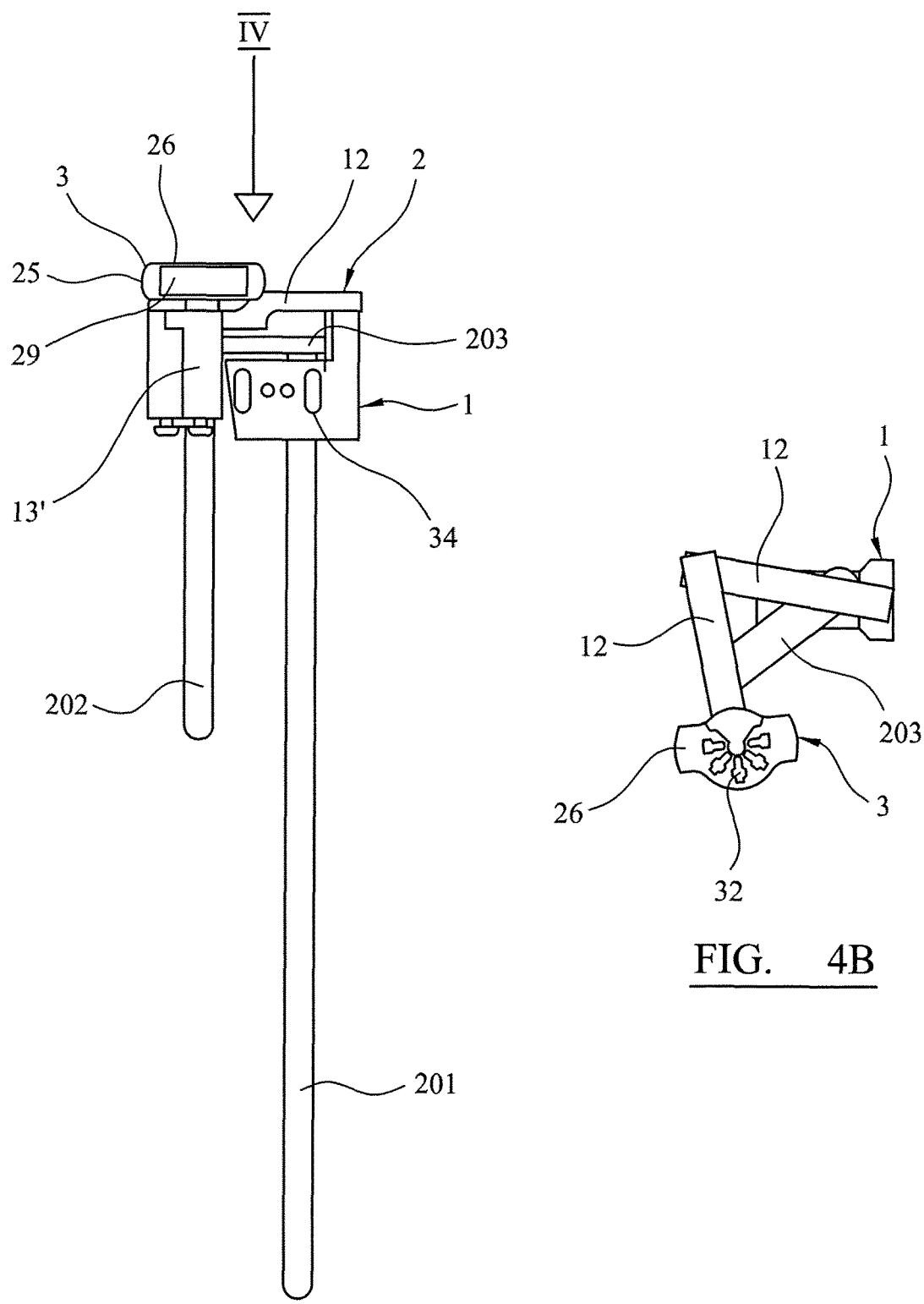
FIG. 4A is a side view.
FIG. 4B is a plan view of the surgical instrument system of FIG. 2 in the direction of arrow IV in FIG. 4A.

FIGS. 1A and 1B illustrate, schematically, an existing cutting tool 102. The cutting tool 102 has a main body portion 103 and a handle 104. Internally of the main body portion 103 includes a drive mechanism such as a drive shaft 205, a motor (not shown) and electrical circuitry for connecting the motor to a power source such as an external battery pack (not shown). The motor is coupled to the drive shaft 105 which is configured to oscillate about an axis of oscillation Y. The cutting tool 102 includes a saw blade 106 with a cutting edge 107 which is typically a serrated distal end of the saw blade 106. The saw blade 106 is secured to the cutting tool 102 at the proximal end 108 of the saw blade 106 for oscillation in a side-to-side motion around the axis of oscillation Y and driven by the oscillating drive shaft 105. The oscillating shaft is provided within a shaft housing 109 at one end of the main body portion 103.

The saw blade 106 is secured to the cutting tool 102 by clamping between two clamping surfaces 110, 111 provided by a plate 112 located at one end of the shaft housing 109 and which is movable between an open and a closed position—as indicated by the double-headed arrow in FIG. 1A.

The proximal end 108 of the saw blade 106 is shaped to include a curved recess 113 and includes a plurality of pierced, shaped apertures 114 which are configured to engage respective pins 115 provide on one of the clamping surfaces 110, 111 of the cutting tool 102. This is illustrated in FIG. 10D.

The clamping surface 111 which carries the pins 115, and the plate 112, are coupled to the oscillating shaft 105 for oscillation about the shaft 105.

With the plate 112 in the open position, the proximal end 108 is inserted into the gap between the two clamping surfaces 100, 111 so that the drive shaft 105 is retained within the curved recess and the apertures 114 are engaged on the pins 115. The plate 112 is then moved to the closed position to clamp the saw blade 106 in place so that oscillation of the drive shaft 105 causes the saw blade 106 to oscillate around the axis of oscillation Y in a plane orthogonal to the axis of oscillation Y.

The configuration of the saw blade 106 and the means by which the saw blade 106 is attached to the cutting tool 102 for oscillation about the axis of oscillation Y will vary depending upon the type of saw blade 106 and the cutting tool 102, as is well known by a person skilled in the art, and the embodiment described herein is by way of example only.

The mounting block 1 is configured for mounting onto a bone surface (not shown) for use in preparing and resecting a bone surface in bone joint replacement surgery.

The mounting block 1 includes a guide surface 4, an underside surface 5 opposite the guide surface 4, end faces 6, 6' and side faces 7, 7'. Running through the mounting block 1 from the guide surface 4 to the underside surface 5 are a plurality of alignment bores 8 which are used to retain an alignment tool 200 as will be described in further detail below. The guide surface defines a guide surface plane.

The alignment bores 8 subtend selected angles, θ, to a plane running orthogonal to the guide surface 4. These alignment bores 8 are used to enable an alignment tool 200 to be angled as required during the surgical procedure. In the embodiment described herein, there are four alignment bores 8 which subtend angles of 0°, 3°, 5° and 7° to a plane orthogonal to the guide surface 4.

The mounting block 1 has a projection 9, which is an extension of one of the end faces 6 and which extends substantially perpendicularly from the guide surface 4 such that the mounting block 1 has an L-shaped cross-sectional profile. The projection 9 has a retaining bore 10 extending through its length and extending through the main body portion of the mounting block 1 through to the underside surface 5.

The mounting block 1 is also provided with a number of elongate and circular apertures 34, 35 used for securing the mounting block 1 to a bone surface using mounting projections (not shown). The elongate and circular apertures 34, 35 are provided on both the projection 9 and the side faces 7, 7'.

The mounting arm 2 is removably attached to the mounting block 1 and configured for movement relative to the mounting block 1 as will be described in further detail below.

The mounting arm 2 comprises one or more U-shaped mounting arm sections 11.

Figure 5A:
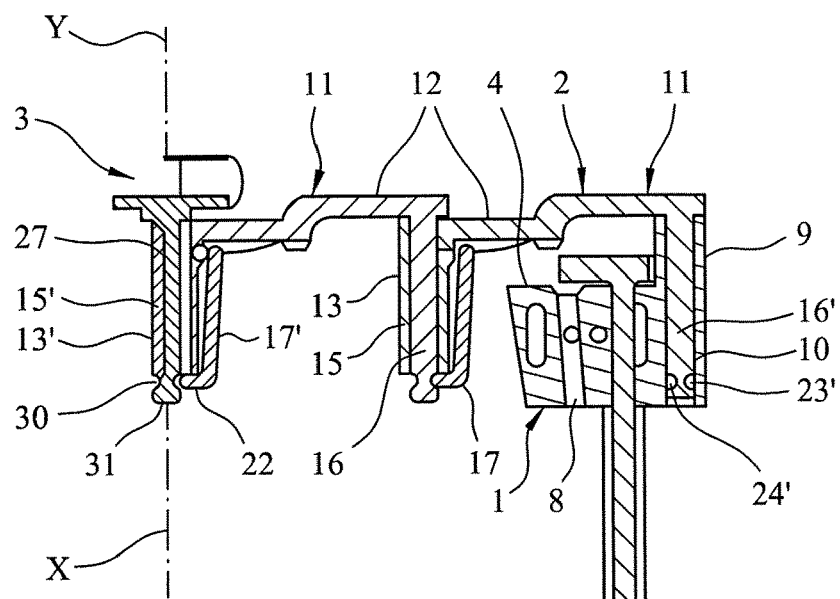
FIG. 5A is an alternative plan view of the surgical instrument system of FIG. 2.
Figure 5B:
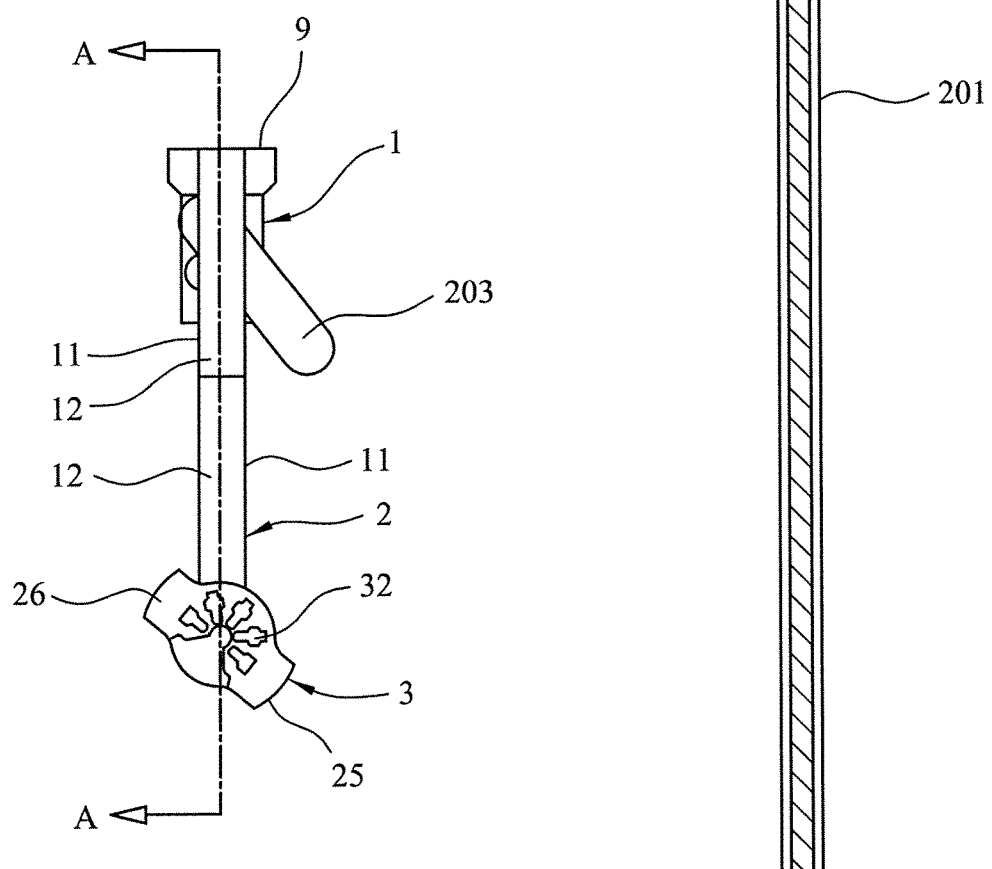
FIG. 5B is a cross-section in the direction of the line A-A in FIG. 5A.
Figure 6:
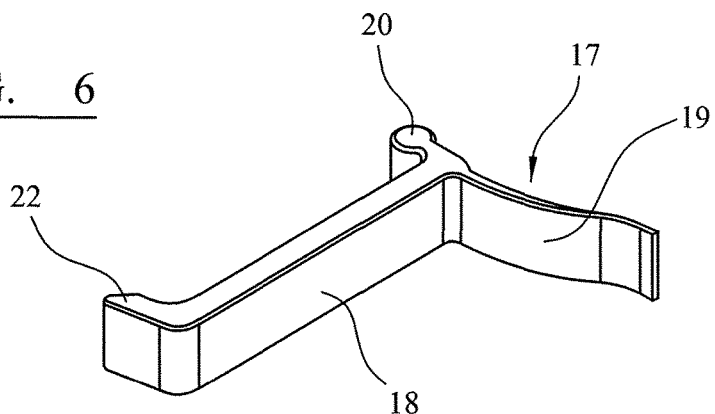
FIG. 6 is a perspective view of an L-shaped locking member used in the cutting guide assembly of FIG. 1.
Figure 7A:
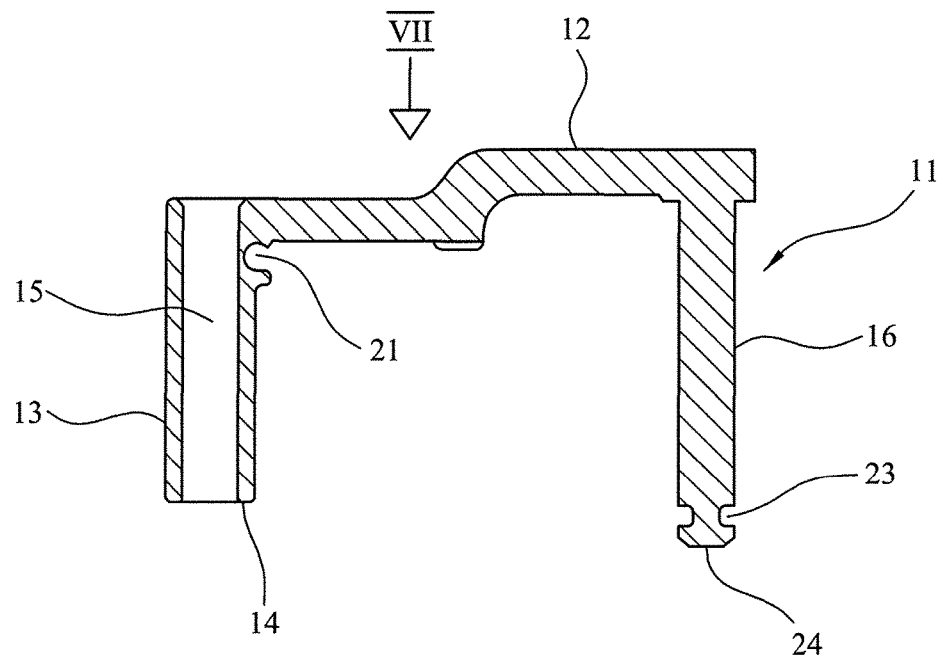
FIG. 7A is a cross-section through a mounting arm section of a mounting arm which forms part of the cutting guide assembly of FIG. 1.
Figure 7B:
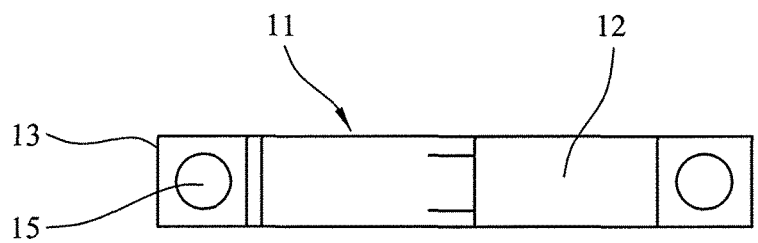
FIG. 7B is a plan view of the mounting arm section of FIG. 7A in the direction of the arrow VII of FIG. 7A.

Each mounting arm section 11 comprises a crosspiece 12 and two substantially parallel posts 13, 16 extending perpendicularly from the crosspiece 12 at each end of the crosspiece 12. Each crosspiece 12 has a kinked or dog-leg shaped profile so that when two mounting arm sections 11 are joined together, as will be described in further detail below, the top reference plane of the mounting arm 2 is retained. This is illustrated in FIG. 5B.

A first post 13 has a longitudinal cylindrical bore 15 running through the length of the first post 13. The other, second, post 16 is cylindrical and solid. A circumferential groove 23 is provided towards the distal end 24 of the second post 16. The second post 16 is longer than the first post 13 so that the circumferential groove 23 is located beyond the plane of the distal end 14 of the first post 13.

Each mounting arm section 11 is provided with an L-shaped locking member 17 attached at the apex between the first post 13 and the crosspiece 12. The L-shaped locking member 17 comprises a locking arm 18 and a resilient biasing member 19. A curved projection 20 is provided at the junction of the locking arm 18 and the biasing member 19.

The apex between the first post 13 and the crosspiece 12 has a curved groove 21 which is configured to receive and retain the curved projection 20 on the L-shaped locking member 17 so that the L-shaped locking member 17 is able to pivot between a locking position and an unlocking position.

The locking arm 18 is provided with a lip or flange 22 at its distal end.

The mounting arm 2 can comprise a single mounting arm section 11 or can be formed by joining two or more mounting arm sections 11 together.

Two or more mounting arm sections 11 are joined together by fully inserting a second post 16 of one mounting arm section 11 into the longitudinal cylindrical bore 15 in the first post 13 of a second mounting arm section 11 as illustrated in FIG. 5B.

Because the second post 16 is dimensioned such that it is longer than the length of the longitudinal cylindrical bore 15 into which it is inserted, the distal end 24 of the second post 16 extends beyond the first cylindrical post 13 such that the circumferential groove 23 of the second post 16 is located outside of the first post 13.

The dimensions of the longitudinal cylindrical bore 15 are such that the second post 16 is snugly received in the longitudinal cylindrical bore 15 so that the second post 16 can freely rotate within the longitudinal bore 15 with minimal lateral play or displacement.

The L-shaped locking member 17 is mounted on the mounting arm section 11 and dimensioned such that the lip 22 of the locking arm 18 can engage with the circumferential groove 23 of the second post 16 when the L-shaped locking member 17 is in the locking position. The resilient biasing member 19 biases the L-shaped locking member 17 in the locking position in which the lip 22 is engaged in the circumferential groove 23, thereby forming a detent to lock the two U-shaped mounting arm sections 11 together. To disengage the lip 22 from the groove 23 the curved resilient biasing member 19 is manually depressed which causes the L-shaped member 17 to pivot within the curved groove 21 thus disengaging the lip 22 from the circumferential groove 23.

The L-shaped locking member 17 thus retains the second post 16 in position within the longitudinal bore 15 while allowing the second post 16 to rotate within the longitudinal bore 15 around the longitudinal axis of the second post 16.

This connection between the two mounting arm sections 11 creates a point of articulation for the mounting arm 2.

If required, further mounting arm sections 11 can be added as required. Adding additional mounting arm sections 11 increases the number of joints of articulation.

The number of mounting arm sections 11 joined together will depend upon the length of the saw blade 106 and the amount of side-to-side displacement required by the surgeon. This can provide enhanced flexibility depending upon surgeon preference. However, increasing the number of articulations significantly can increase the risk of alignment error. The use of one or two mounting arm sections 11 is therefore preferred.

When the required number of mounting arm sections 11 are coupled together, a mounting arm 2 is formed which has a first end and a second end, with a first post 13' extending from the first end in a direction substantially perpendicularly to the mounting arm 2 and a second post 16' extending substantially parallel to the first post 13' at the second end in the same perpendicular direction. The mounting arm 2 has no, or at least one, point of articulation. The first post 13' has a longitudinal bore 15' running through its length and the second post 16' includes a circumferential groove 23' at the distal end 24'.

The attachment component 3 is used to attach the cutting tool 102 to the cutting guide assembly 1.

Figure 8:
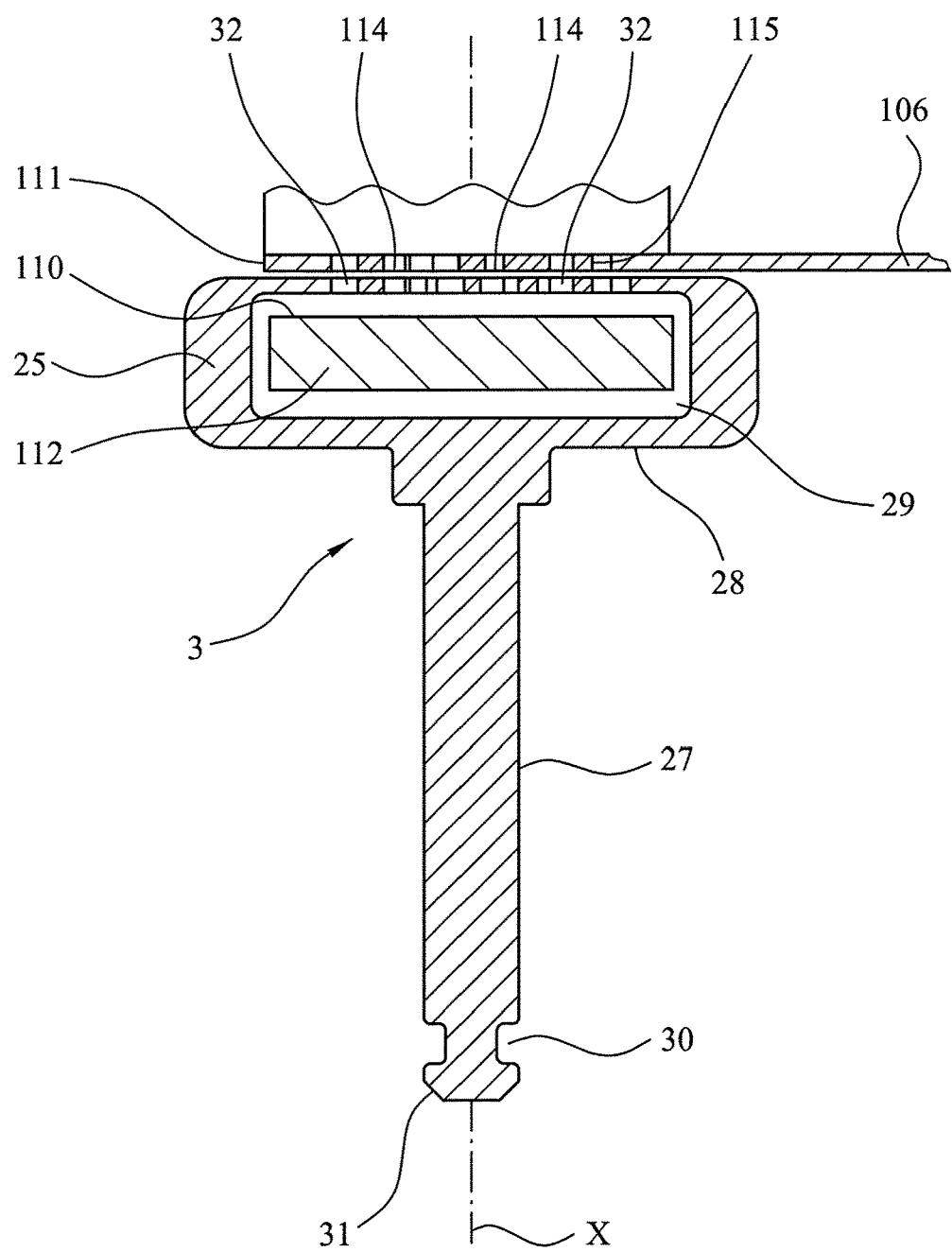
FIG. 8 is a cross-section through the cutting tool attachment member of the cutting guide assembly as attached to the plate of the cutting tool of FIGS. 1A and 1B.
Figure 12A:
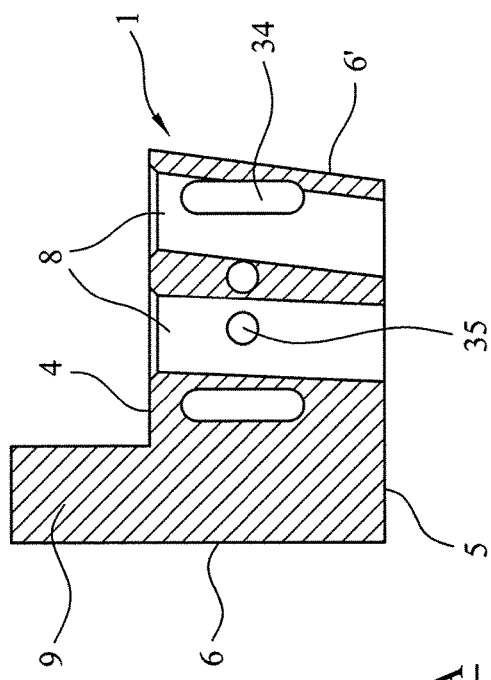
FIG. 12A is a cross-section along the line A-A of FIG. 11.
Figure 12B:
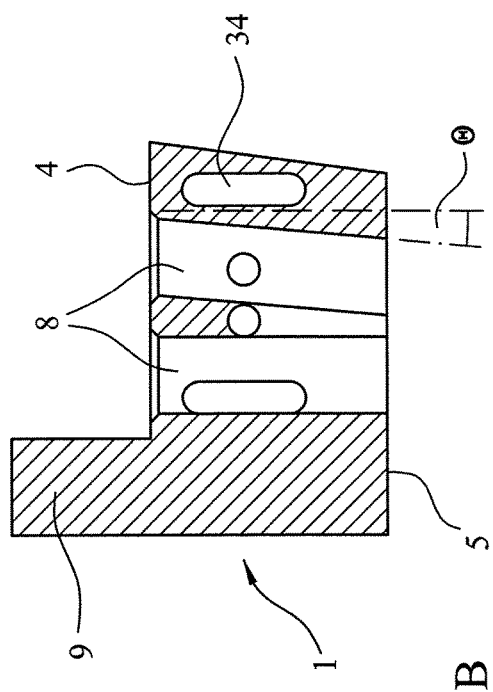
FIG. 12B is a cross-section along the line A-A of FIG. 11.
Figure 11:
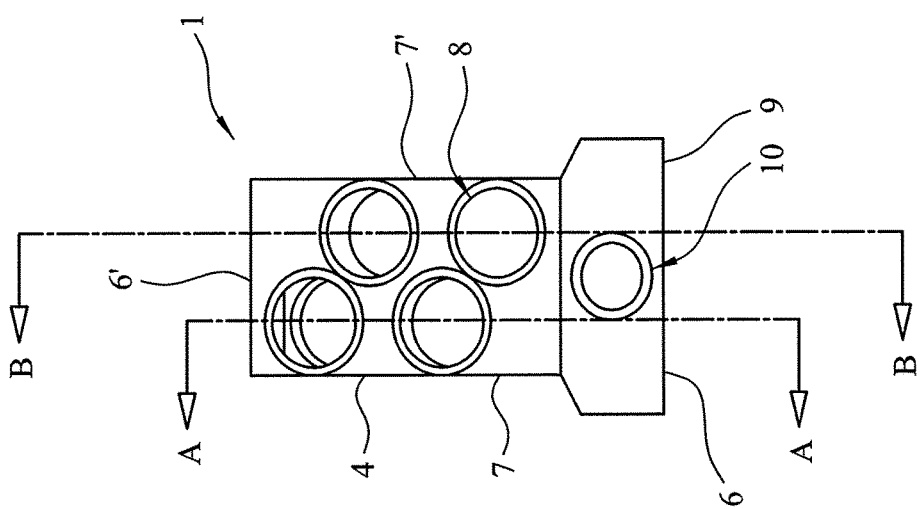
FIG. 11 is a plan view of the mounting block of the cutting guide assembly.

The attachment component 3 comprises an attachment block 25 which defines a first, attachment surface 26 and a second, underside surface 28. A cylindrical shaft 27 extends from the second surface 28 in a perpendicular direction, away from the first surface 26. The attachment component 3 has a T-shaped cross section as illustrated in FIG. 8.

In the embodiment described herein, the attachment block 25 is hollow to define an internal cavity 29. The internal cavity 29 is provided to receive the plate 112 of the cutting tool 102 when the cutting tool 102 is mounted on the guide assembly 100 as can be seen on schematically in FIG. 8.

The first surface 26 includes a number of pierced apertures 32 to match corresponding apertures 114 in the proximal end 108 of the saw blade 106. The actual arrangement of apertures (if any) will depend upon the shape and configuration of the saw blade 106 and how the saw blade 106 is attached to the main body of the cutting tool 102 for operation.

The first surface 26 includes a recessed portion 33.

It will be understood by a person skilled in the art that the attachment component 3 can have any suitable arrangement of attachment means that enables the saw blade 106 to connect to the drive mechanism of the cutting tool 102 while enabling the saw blade 106 to be retained against the attachment component 3 for usual oscillation around the axis of oscillation Y as will be described below. The arrangement of recesses and pierced apertures described herein is only one way of achieving this and is relevant for the version of the cutting tool described herein.

The cylindrical shaft 27 is located substantially centrally of the attachment block 25, and therefore of the attachment component 3, such that the longitudinal axis X of the attachment component 3 is collinear with the longitudinal axis of the cylindrical shaft 27.

In this way, when the saw blade 106 is retained against the first surface 26 of the attachment block 25, the longitudinal axis X of the cylindrical shaft 27 is collinear with the axis of oscillation Y of the saw blade 106.

The cylindrical shaft 27 has a circumferential groove 30 provide towards the distal end 31 of the cylindrical shaft 27. The cylindrical shaft 27 is similar in shape and dimension to the second cylindrical post 16' of the mounting arm 2 and is configured for insertion into the longitudinal bore 15' of the first cylindrical post 13' of the mounting arm 2, such that the lip 22 of a respective L-shaped locking member 17 engages with the circumferential groove 30 to retain the cylindrical shaft 27 in place when inserted, while allowing relative rotation of the cylindrical shaft 27 within the longitudinal cylindrical bore 15'.

The attachment component 3 is therefore attached to the mounting arm 2 by fully inserting the cylindrical shaft 27 into the longitudinal cylindrical bore 15' in the respective first post 13' and locking it into place by means of the L-shaped locking member 17.

The shaft 27 and longitudinal cylindrical bore 15' are all dimensioned so that they cooperate together as described above, so as to rotate or pivot around their respective longitudinal axes with respect to each other with minimal lateral play or displacement relative to each other. There will also be minimal axial displacement as the detent provided by the L-shaped locking member, along with gravity, serves to keep the shaft 27 inserted into the longitudinal bore of the first post 13'.

To fully assemble the cutting guide assembly 100, the attachment component 3 is attached to the mounting arm 2 as described above, and the mounting arm 2 is mounted onto the mounting block 1 by means of engagement of the free second post 16' and the retaining bore 10 of the mounting block 1.

As with the other points of connection, the second post 16' and the retaining bore 10 are dimensioned so that they cooperate together as described above, so as to rotate or pivot with respect to each other with minimal lateral play or displacement relative to each other. Gravity assists in keeping the second post 16' in the retaining bore 10 to minimise axial movement.

The cutting guide assembly 100 is used with an alignment tool 200 to provide a surgical instrument system.

The alignment tool 200 comprises first and second substantially parallel alignment rods 201, 202 separated by a cross-piece 203. The first alignment rod 201 is longer than the second alignment rod 202.

In use, the mounting block 1 is loosely fixed to the bone adjacent the surface to be prepared and resected, by means of a single mounting projection in the form of a pin (not shown) inserted through one of the elongate or circular apertures 34, 35 and into the bone.

The mounting block 1 can be affixed to the bone surface by means of the elongate or circular apertures 34, 35 provide on the end face 6 or on the side faces 7, 7' so that either a side face 7, 7' or an end face 6 abuts the bone surface. The orientation and position will be selected according to surgeon preference and/or bone surface to be prepared.

In the example of a tibial resection during knee prosthesis surgery, the mounting block 1 will be affixed toward the knee joint at the top of the tibia. If required, and in accordance with surgeon preference, a stylus can be used as is well known in the art.

To ensure that the mounting block 1 is correctly positioned on the bone the alignment tool 200 is used.

One of the alignment rods 201, 202 is placed into one of the alignment bores 8 at the required angle so that the other alignment rod 201, 202 is pointed at an appropriate reference point, such as the second toe of the patient when performing a tibial resection. Preferably, the longer alignment rod 201 is used for alignment with the toe. The second toe is used to set varus/valgus angle of the cut. The surgeon can examine the alignment of the rod 201 to the patient's proximal tibial surface to make sure they have it parallel, and this will get the tibial posterior slope setting correct according to the selected alignment bore 8. The alignment rod 201 can be used with an additional ankle clamp or brace to help the surgeon reference the malleoli.

Alternatively, the longer rod 201 can be inserted through a drilled opening into the intramedullary canal of the tibia or femur, allowing the surgeon to guide the cut from an intramedullary reference.

When the mounting block 1 is determined to be in the correct position, then the mounting block 1 is securely fixed by means of further mounting projections (not shown) in one or more of the circular and/or elongate apertures 34, 35.

Once the mounting block 1 is fastened securely, then the mounting arm 2 can be mounted on to the mounting block 1 at the second end, by inserting the second post 16' into the retaining bore 10.

Prior to, or after, mounting the mounting arm 2 onto the mounting block 1, the cutting tool 102 needs to be mounted onto the first end of the mounting arm 2 to form the full cutting guide assembly 100 in situ.

To mount the cutting tool 102 onto the guide assembly 100 at the first end of the mounting arm 2, the plate 112 of the cutting tool 102 is moved to the open position and the saw blade 106 removed. The saw blade 106 is placed on the first surface 26 of the attachment block 25 so that the curved recess 113 and the shaped apertures 114 are coincident with the recessed portion 33 and pierced apertures 32 on the first surface 26 of the attachment block 25. This is shown, for example, in FIG. 10D.

The saw blade 106 and the attachment component 3 are then attached to the cutting tool 102 by sliding the plate 112 into the internal cavity 29 and then moving the plate 112 to the closed position so that the saw blade 106, and the top surface 26 of the attachment block 25 are clamped on the cutting tool 102 by means of the clamping of the first surface 26 and the saw blade 106 between the two clamping surfaces 110, 111.

The attachment component 3 is attached to the mounting arm 2 at the first end by inserting the shaft 27 into the longitudinal bore 15' in the first post 13'.

The attachment of the various components of the cutting guide assembly 100, the cutting tool 102 and the saw blade 106 can generally be done in any order in accordance with surgeon preference.

As described above, the shaft 27 is secured within the longitudinal bore 15' of the first post 13'. The lip 22 is disengaged in the same way and as described above so that the attachment component 3 can be removed when required. The L-shaped locking member 17 retains the second post 16 in position while allowing it to rotate around its longitudinal axis.

Once the cutting guide assembly 100 is fully assembled with the mounting block 1 secured to the bone surface and the cutting tool 102 mounted onto the cutting guide assembly 100, then the cutting tool 102 can be used to prepare the bone surface.

The alignment of the second post 16' of the mounting arm 2 in the retaining bore 10 configures the second post 16' of the mounting arm 2 to be perpendicular to the guide surface 4 of the mounting block 1.

As described above, the shaft 27 is located substantially centrally of the attachment block 25, and therefore of the attachment component 3. The attachment component 3 thus has a longitudinal axis X which is collinear with the longitudinal axis of the cylindrical shaft 27.

In this way, when the saw blade 106 is retained against the first surface 26 of the attachment component 3, the longitudinal axis X of the shaft 27, and the longitudinal axis of the longitudinal bore 15', are collinear with the axis of oscillation Y of the saw blade 106. This is illustrated in FIG. 5B.

The longitudinal bore 15' runs parallel to the second post 16' and, consequently the axis of oscillation Y of the saw blade 106 is substantially parallel to the longitudinal axis of the second post 16' which means that the plane of oscillation of the saw blade 106 is parallel to, but displaced from, the guide surface 4 of the mounting block 2.

In this way, a surgeon is able to prepare and resect a bone surface using a cutting tool 102 using a guide assembly which guides the saw blade 106 in a direction which is parallel to the guide surface 4 but without the guide surface 4 being in contact with the saw blade 106 itself, with the attendant problems discussed above.

The articulated mounting arm 2 enables the saw blade 106 to be moved from side-to-side and to and away from the bone without the saw blade 106 moving out of the selected plane of oscillation.

FIGS. 10A to 10D illustrate the way in the cutting guide assembly 100 can be moved in selected directions in this way.

Variants are possible within the scope of the present invention. For example, other cutting tools can be used with the attachment component for mounting the cutting tool on the guide assembly 100 being adapted accordingly.

In an alternative embodiment, the retaining bore 10 could be provided with a number of substantially axially spaced retention mechanisms such as resilient lips (not shown) that are configured to engage with the circumferential groove 23 of the second post 16' of the mounting arm 2 that is configured to retain the second post 16' at a particular position within the retaining bore 10 so that the height of the mounting arm 2 relative to the guide surface 4 of the mounting block 1 can be adjusted. This can be used, for example, to support a stylus (not shown) for use in determining the correct plane for bone surface preparation.

I claim:

1. A cutting guide assembly for guiding a saw blade of a cutting tool, the saw blade being configured for oscillation in a plane of oscillation, and around an axis of oscillation, the guide assembly comprising:
   a mounting block having a guide surface;
   a mounting arm having a first end and a second end;
   a first post, having a longitudinal axis, extending from the first end of the mounting arm in a direction perpendicular to the mounting arm and configured to be retained in the mounting block in a direction perpendicular to the guide surface;
   a second post extending parallel to the first post at the second end; and
   a cutting tool attachment component for attaching the cutting tool to the cutting guide assembly, the cutting tool attachment component having a first surface against which the saw blade can be retained for oscillation around the axis of oscillation, and a shaft, having a longitudinal axis, extending in a direction away from, and perpendicular to, the first surface and configured to cooperate with the second post such that the longitudinal axis of the shaft is collinear with the axis of oscillation of the saw blade, and such that, when the saw blade is retained against the first surface, the plane of oscillation is parallel to, and displaced from, the guide surface of the mounting block.

2. The cutting guide assembly of claim 1, wherein the mounting block includes an elongate retaining bore running through the block in a direction perpendicular to the guide surface so as to retain the first post in the mounting block such that the longitudinal axis of the first post extends in a direction perpendicular to the guide surface.

3. The cutting guide of claim 2, wherein the retaining bore includes at least one retaining mechanism for retaining the first post within the retaining bore at a predetermined position.

4. The cutting guide assembly of claim 1, wherein the second post further includes a longitudinal bore configured to receive and retain the shaft of the cutting tool attachment member so that the longitudinal axis of the shaft is collinear with the axis of oscillation of the saw blade.

5. The cutting guide assembly of claim 4, wherein the shaft has a distal end and includes a circumferential groove provided towards the distal end of the shaft, and the mounting arm includes a detent provided adjacent the second post, the detent comprising a spring-biased locking member having a lip which engages with the circumferential groove provided on the shaft.

6. The cutting guide assembly of claim 1, wherein the mounting arm includes an articulation.

7. The cutting guide assembly of claim 6, wherein the mounting arm comprises two or more U-shaped mounting arm sections detachably coupled to each other to provide the articulation.

8. The cutting guide assembly of claim 7, wherein at least one of the U-shaped mounting arm sections includes a detent comprising a spring-biased locking member having a lip, and another of the two or more U-shaped mounting arm sections includes a cooperating post with a circumferential groove provided thereon, such that the mounting arm sections are detachably secured together by means of engagement of the lip with the circumferential groove provided on one the another of the two or more U-shaped mounting arm sections.

9. The cutting guide assembly of claim 1, wherein the mounting block comprises a plurality of alignment bores running through the mounting block from the guide surface and configured to receive an alignment rod of an alignment tool.

10. The cutting guide assembly of claim 1 wherein the cutting guide assembly is part of a kit including an alignment tool alignment tool comprising a cross-piece and first and second substantially parallel alignment rods provided at the ends of the cross piece.

11. A cutting guide assembly for guiding a saw blade of a cutting tool, the saw blade being configured for oscillation in a plane of oscillation, and around an axis of oscillation, the guide assembly comprising:
   a mounting block having a guide surface, the mounting block further including an elongate retaining bore running through the block in a direction perpendicular to the guide surface;
   a mounting arm having a first end and a second end;
   a first post, having a longitudinal axis, extending from the first end of the mounting arm in a direction perpendicular to the mounting arm such that the longitudinal axis of the first post extends in a direction perpendicular guide surface; the first post being retained in the elongate retaining bore of the mounting block such that the first post extends in a direction perpendicular to the guide surface;
   a second post extending parallel to the first post at the second end; and a cutting tool attachment component for attaching the cutting tool to the cutting guide assembly, the cutting tool attachment component having a first surface against which the saw blade can be retained for oscillation around the axis of oscillation, and a shaft, having a longitudinal axis, extending in a direction away from, and perpendicular to, the first surface and configured to cooperate with the second post such that the longitudinal axis of the shaft is collinear with the axis of oscillation of the saw blade, and such that, when the saw blade is retained against the first surface, the plane of oscillation is parallel to, and displaced from, the guide surface of the mounting block.

12. The cutting guide assembly of claim 11, wherein the retaining bore includes at least one retaining mechanism for retaining the first post within the retaining bore at a predetermined position.

13. The cutting guide assembly of claim 11, wherein the second post further includes a longitudinal bore configured to receive and retain the shaft of the cutting tool attachment member so that the longitudinal axis of the shaft is collinear with the axis of oscillation of the saw blade.

14. The cutting guide assembly of claim 13, wherein the shaft includes a circumferential groove provided towards the distal end of the shaft, and the mounting arm includes a detent provided adjacent the second post, the detent comprising a spring-biased locking member having a lip which engages with the circumferential groove provided on the shaft.

15. A surgical instrument system including a cutting guide assembly for guiding a saw blade of a cutting tool, the saw blade being configured for oscillation in a plane of oscillation, and around an axis of oscillation, and an alignment tool;

the cutting guide assembly comprising:
a mounting block having a guide surface, the guide surface;
a mounting arm having a first end and a second end;
a first post, having a longitudinal axis, extending from the first end of the mounting arm in a direction perpendicular to the mounting arm and configured to be retained in the mounting block in a direction perpendicular to the guide surface;
a second post extending parallel to the first post at the second end; and a cutting tool attachment component for attaching the cutting tool to the cutting guide assembly, the cutting tool attachment component having a first surface against which the saw blade can be retained for oscillation around the axis of oscillation, and a shaft, having a longitudinal axis, extending in a direction away from, and perpendicular to, the first surface and configured to cooperate with the second post such that the longitudinal axis of the shaft is collinear with the axis of oscillation of the saw blade, and such that, when the saw blade is retained against the first surface, the plane of oscillation is parallel to, and displaced from, the guide surface of the mounting block; and
the alignment tool comprising a cross-piece and first and second substantially parallel alignment rods provided at the ends of the cross piece.

* * * * *